United States Patent
Liao et al.

(10) Patent No.: US 11,424,021 B2
(45) Date of Patent: Aug. 23, 2022

(54) MEDICAL IMAGE ANALYZING SYSTEM AND METHOD THEREOF

(71) Applicant: National Taiwan University, Taipei (TW)

(72) Inventors: Wei-Chih Liao, Taipei (TW); Wei-Chung Wang, Taipei (TW); Kao-Lang Liu, Taipei (TW); Po-Ting Chen, Taipei (TW); Ting-Hui Wu, Taipei (TW); Holger Roth, Taipei (TW)

(73) Assignee: National Taiwan University, Taipei (TW)

( * ) Notice: Subject to any disclaimer, the term of this patent is extended or adjusted under 35 U.S.C. 154(b) by 195 days.

(21) Appl. No.: 16/868,742

(22) Filed: May 7, 2020

(65) Prior Publication Data
US 2020/0357506 A1 Nov. 12, 2020

Related U.S. Application Data

(60) Provisional application No. 62/845,922, filed on May 10, 2019.

(30) Foreign Application Priority Data

Apr. 21, 2020 (TW) .................. 109113320

(51) Int. Cl.
*G06K 9/00* (2022.01)
*G16H 30/40* (2018.01)
(Continued)

(52) U.S. Cl.
CPC ............... *G16H 30/40* (2018.01); *G06N 3/08* (2013.01); *G06T 7/0012* (2013.01); *G06T 7/11* (2017.01);
(Continued)

(58) Field of Classification Search
CPC .................................................... G16H 30/40
See application file for complete search history.

(56) References Cited

U.S. PATENT DOCUMENTS

| 9,486,142 B2 | 11/2016 | Hielscher et al. |
| 2014/0105471 A1* | 4/2014 | Brown ............... G06T 7/11 382/128 |

(Continued)

FOREIGN PATENT DOCUMENTS

| CN | 107767362 | 3/2018 |
| CN | 109584252 | 4/2019 |

(Continued)

OTHER PUBLICATIONS

Liao, et al. "Differentiation Between Pancreatic Cancer and Normal Pancreas on Computed Tomotraphy with Artificial Intelligence", A. Gastroenterology supplement to DDW, vol. 156, Issue 6, Supplement 1, p. S-59, https://www.gastrojournal.org/issue/S0016-5085(19)X6001-1?page=3.

(Continued)

*Primary Examiner* — Hadi Akhavannik
(74) *Attorney, Agent, or Firm* — Amin, Turocy & Watson, LLP

(57) ABSTRACT

Provided are a medical image analyzing system and a method thereof, which mainly crop a plurality of image patches from a processed image including a segmentation label corresponding to a location of an organ, train a deep learning model with the image patches to obtain prediction values, and plot a receiver operating characteristic curve to determine a threshold which determines whether the image patches are cancerous, thereby effectively improving the detection rate of cancer.

18 Claims, 10 Drawing Sheets

(51) Int. Cl.
  *G16H 50/20* (2018.01)
  *G06T 7/00* (2017.01)
  *G06N 3/08* (2006.01)
  *G06T 7/11* (2017.01)

(52) U.S. Cl.
  CPC ... *G16H 50/20* (2018.01); *G06T 2207/10088* (2013.01); *G06T 2207/20132* (2013.01); *G06T 2211/40* (2013.01)

(56) References Cited

U.S. PATENT DOCUMENTS

| | | | | |
|---|---|---|---|---|
| 2014/0149112 A1* | 5/2014 | Kalinli-Akbacak | .... | G10L 15/04 704/232 |
| 2014/0322354 A1* | 10/2014 | Goel | .... | C12Q 1/6886 424/649 |
| 2017/0076448 A1* | 3/2017 | Chen | .... | G06K 9/00147 |
| 2018/0315188 A1* | 11/2018 | Tegzes | .... | G06K 9/2054 |
| 2019/0080450 A1* | 3/2019 | Arar | .... | G06T 7/0012 |
| 2019/0114770 A1* | 4/2019 | Song | .... | G06T 7/0014 |

FOREIGN PATENT DOCUMENTS

| | | |
|---|---|---|
| TW | I587844 | 6/2017 |
| TW | 201839128 | 11/2018 |

OTHER PUBLICATIONS

Liao, et al. "Differentiation Between Pancreatic Cancer and Normal Pancreas on Computed Tomotraphy with Artificial Intelligence", Digestive Disease Week, San Diego, CA/ May 18-21, 2019, https://ddw.org/home.

Taiwanese Office Action for Taiwanese Patent Application No. 109113320 dated May 24, 2021.

\* cited by examiner

MEDICAL IMAGE ANALYZING SYSTEM AND METHOD THEREOF

BACKGROUND

1. Technical Field

The present disclosure relates to an image analyzing system and a method thereof, particularly to a medical image analyzing system and a method thereof.

2. Description of Related Art

In current medical standards, pancreatic cancer is one of the cancers that are difficult to detect early, and once the tumor size exceeds 2 cm, the survival rate drops significantly. In the related art, computed tomography (CT) imaging is currently the main method for detecting and evaluating pancreatic cancer. However, the detection efficiency still depends on the personal experience of the radiologist. For example, about 40% of the tumors smaller than 2 cm cannot be detected. This reflects that manual image reading and determination is too subjective, and it is easy to cause misjudgment due to human factors.

Therefore, how to provide a medical image analyzing system and a method thereof applicable to identifying pancreatic cancer to improve the detection rate, for example, has become an urgent issue in the art.

SUMMARY

The present disclosure is to provide a medical image analyzing system, including: an image preprocessing module configured to process at least one image including an organ to generate at least one processed image, wherein the processed image includes a segmentation label corresponding to a location of the organ; a patch cropping module configured to crop a plurality of image patches from the processed image including the segmentation label; an analysis module configured to train a deep learning model with the image patches to obtain a plurality of first prediction values respectively corresponding to each of the image patches; and a threshold selection module configured to plot the first curve according to the first prediction values and determine the first threshold according to the first curve to determine whether each of the image patches is cancerous.

The present disclosure is also to provide a medical image analyzing method, including: processing at least one image including an organ to generate at least one processed image, wherein the processed image includes a segmentation label corresponding to a location of the organ; cropping a plurality of image patches from the processed image including the segmentation label; training a deep learning model with the image patches to obtain a plurality of first prediction values respectively corresponding to each of the image patches; and plotting the first curve according to the first prediction values and determining the first threshold according to the first curve to determine whether each of the image patches is cancerous.

In the aforementioned medical image analyzing system and the method thereof, the patch cropping module crops the image patches from the processed image according to a square window moving along an x-axis and a y-axis of the processed image including the segmentation label.

In the aforementioned medical image analyzing system and the method thereof, the image patches do not overlap with each other or the image patches partially overlap with each other.

In the aforementioned medical image analyzing system and the method thereof, an area of the overlapping part between two of the image patches ranges from 20% to 80% of a total area of each of the image patches.

In the aforementioned medical image analyzing system and the method thereof, the analysis module uses a convolution neural network to train the deep learning model.

In the aforementioned medical image analyzing system and the method thereof, the first curve is a receiver operating characteristic curve and the first threshold is a threshold yielding a maximum value of a Youden index.

In the aforementioned medical image analyzing system and the method thereof, the image is a two-dimensional (2D) image or a three-dimensional (3D) image generated by computed tomography (CT) or magnetic resonance imaging (MRI).

The aforementioned medical image analyzing system and the method thereof further include: a computer-aided diagnosis module configured to input at least one patient image to the image preprocessing module and the patch cropping module to generate a plurality of image patches and input the image patches to the deep learning model to obtain a plurality of first prediction values corresponding to each of the image patches respectively.

In the aforementioned medical image analyzing system and the method thereof, the computer-aided diagnosis module controls the threshold selection module to calculate at least one second prediction value corresponding to the at least one patient image according to the first prediction values corresponding to the image patches generated from the at least one patient image and plot the second curve according to the at least one second prediction value to determine a second threshold according to the second curve to determine whether the at least one patient image harbors cancer.

In the aforementioned medical image analyzing system and the method thereof, for each of the at least one second prediction values, the second prediction value is a ratio between a number of image patches generated from at least one patient image of a patient that are classified as cancerous by applying the first threshold to the first prediction values corresponding to all image patches generated from the at least one patient image of the patient and a total number of all of the image patches generated from the at least one patient image of the patient.

In the aforementioned medical image analyzing system and the method thereof, the second curve is a receiver operating characteristic curve and the second threshold is a threshold yielding a maximum value of a Youden index.

In summary, the medical image analyzing system and the method thereof of the present disclosure have a higher sensitivity than radiologists in identifying pancreatic cancer, which means that the medical image analyzing system and the method thereof of the present disclosure can effectively assist radiologists to reduce their miss rate of clinical diagnosis, e.g., in the case of tumors smaller than 2 cm in size, so that they can effectively improve the situation that about 40% of tumors smaller than 2 cm are not detected.

BRIEF DESCRIPTION OF THE DRAWINGS

The present disclosure can be more fully understood by reading the following description of the embodiments, with reference made to the accompanying drawings, wherein.

DETAILED DESCRIPTION

The following describes the implementation of the present disclosure by particular specific embodiments, and those skilled in the art can easily understand other advantages and effects of the present disclosure based on the contents disclosed in this specification, or implement or apply the present disclosure based on other different specific embodiments.

Figure 1A:
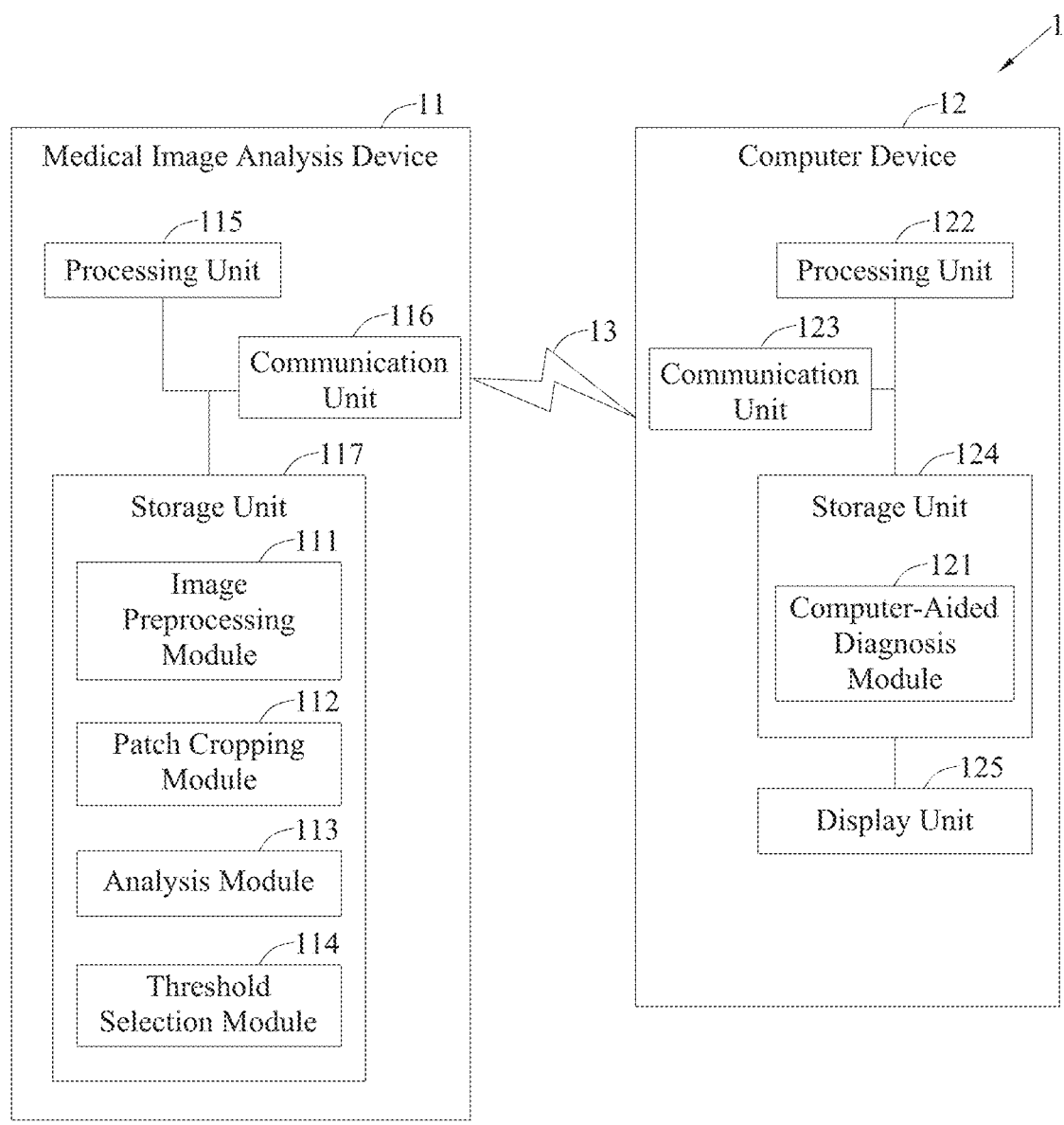
FIG. 1A is a schematic diagram illustrating the first embodiment of a medical image analyzing system of the present disclosure.

FIG. 1A is a schematic diagram illustrating the first embodiment of a medical image analyzing system of the present disclosure. The medical image analyzing system 1 may include a medical image analysis device 11 and a computer device 12 electrically connected to the medical image analysis device 11, wherein the medical image analysis device 11 and the computer device 12 communicate with each other through a wired or wireless network 13.

The medical image analysis device 11 includes an image preprocessing module 111, a patch cropping module 112, an analysis module 113 and a threshold selection module 114, and further includes a processing unit 115, a communication unit 116 and a storage unit 117, wherein the communication unit 116 and the storage unit 117 are coupled to the processing unit 115. In addition, the medical image analysis device 11 may be for example a mobile phone, a tablet computer, a notebook computer, a desktop computer, a server or a cloud server, and the present disclosure is not limited thereto. Moreover, the medical image analysis device 11 may further include for example a display unit of a screen or a monitor (not shown).

In an embodiment, the processing unit 115 may be a central processing unit (CPU), a microprocessor, a graphics processing unit (GPU), or an application-specific integrated circuit (ASIC). The communication unit 116 may be a component supporting signal transmission of various mobile communication systems (e.g., GSM, PHS, CDMA, WCDMA, LTE, WiMAX, 4G, 5G, etc.), Wi-Fi systems, Bluetooth systems or Ethernet. The storage unit 117 may be a fixed or movable storage component of any type, such as random access memory (RAM), read-only memory (ROM), flash memory, hard disk, soft disk, database, or a combination of the aforementioned components or similar components, but the present disclosure is not limited thereto.

In an embodiment, the image preprocessing module 111, the patch cropping module 112, the analysis module 113 and the threshold selection module 114 may be respectively a program code segment, software or firmware stored in the storage unit 117, and may be executed by the processing unit 115, but the present disclosure is not limited thereto. The image preprocessing module 111, the patch cropping module 112, the analysis module 113 and the threshold selection module 114 in the medical image analysis device 11 may also be implemented in a form of other hardware or a hybrid of hardware and software.

The computer device 12 may include a computer-aided diagnosis module 121 and further include a processing unit 122, a communication unit 123, a storage unit 124 and a display unit 125. In an embodiment, the processing unit 122, the communication unit 123 and the storage unit 124 may be components the same as or similar to the aforementioned processing unit 115, communication unit 116 and storage unit 117, respectively. Similarly, the computer-aided diagnosis module 121 may be a program code segment, software or firmware stored in the storage unit 124, and may be implemented in a form of other hardware or a hybrid of hardware and software, and may be executed by the processing unit 122. In addition, the computer device 12 may be for example a mobile phone, a tablet computer, a notebook computer or a desktop computer, etc. The display unit 125 may be a screen or a monitor, but the present disclosure is not limited thereto.

Figure 1B:
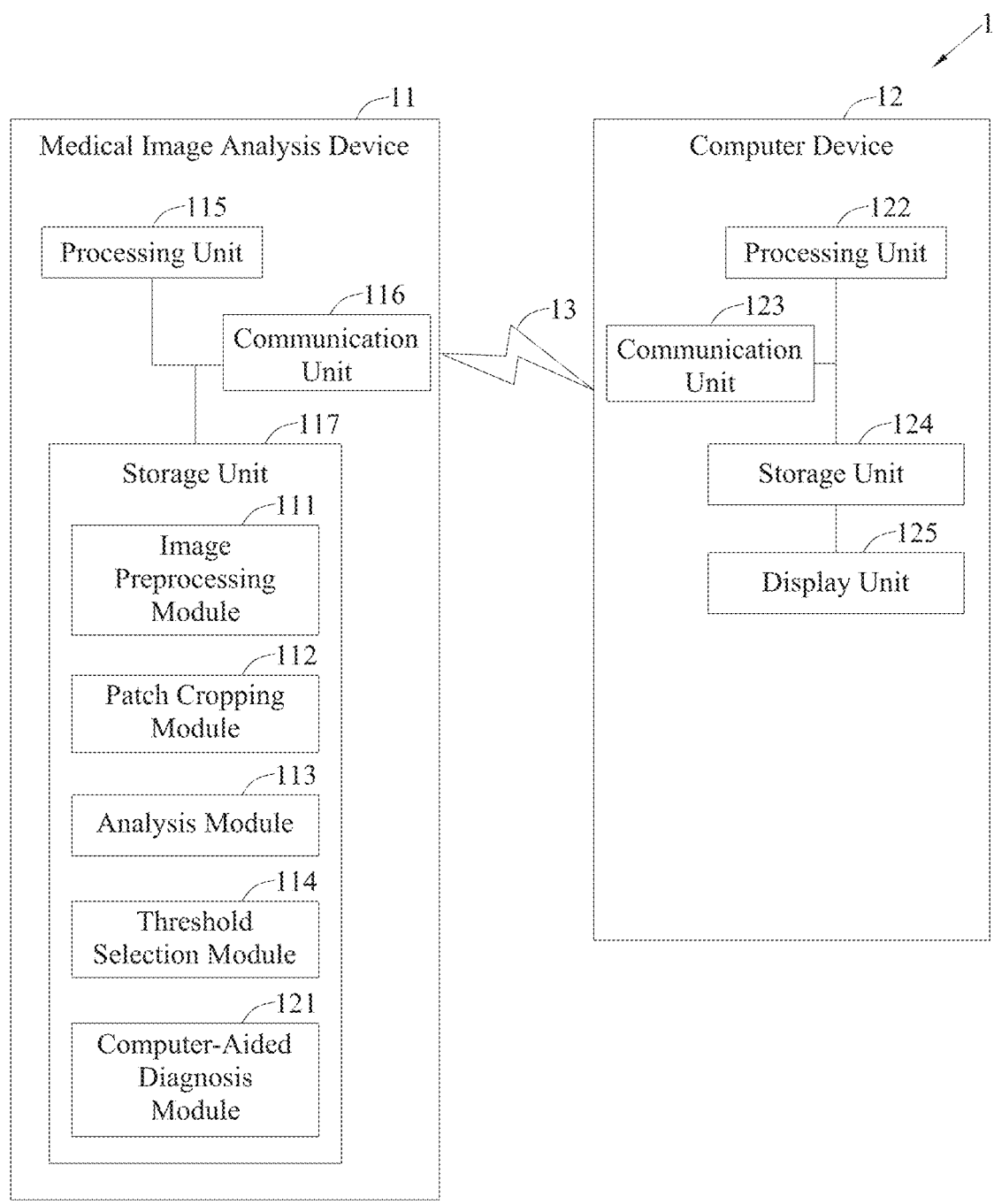
FIG. 1B is a schematic diagram illustrating the second embodiment of a medical image analyzing system of the present disclosure.

Referring to FIG. 1B, which is a schematic diagram illustrating the second embodiment of a medical image analyzing system of the present disclosure. The difference between the second embodiment and the aforementioned first embodiment is that the computer-aided diagnosis module 121 is in the medical image analysis device 11, not in the computer device 12. Therefore, all operations can be performed on the medical image analysis device 11, and the computer device 12 may become a device simply receiving and displaying the output from the medical image analysis device 11, so that the computer device 12 does not need high-end hardware.

Figure 1C:
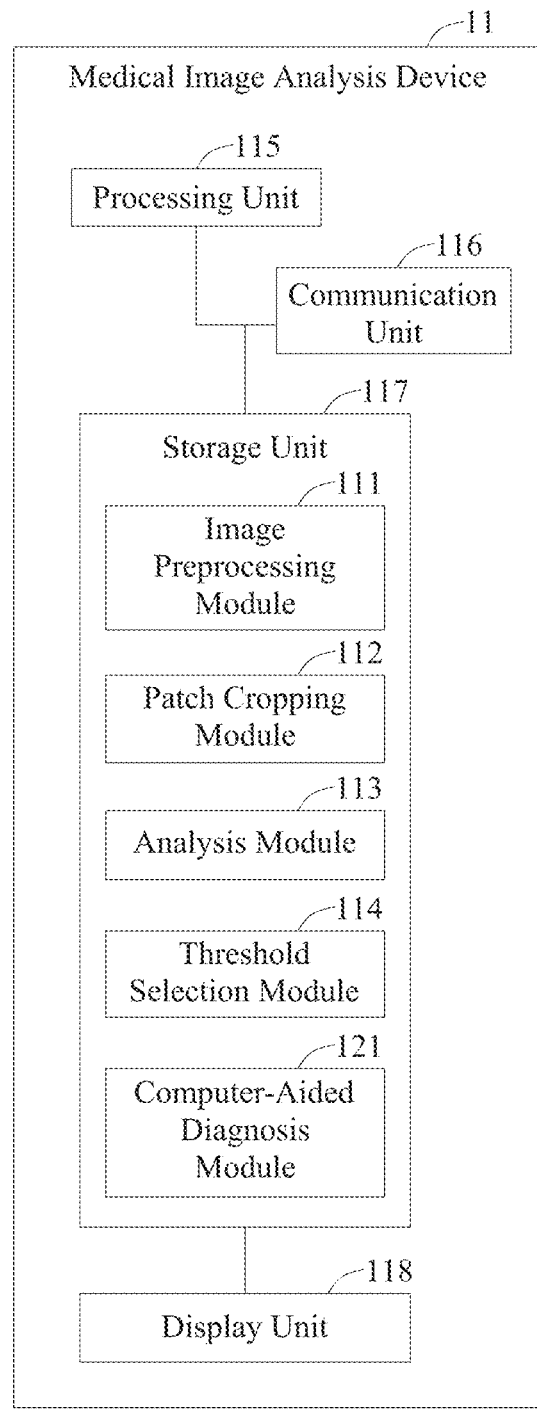
FIG. 1C is a schematic diagram illustrating the third embodiment of a medical image analyzing system of the present disclosure.

Referring to FIG. 1C, which is a schematic diagram illustrating the third embodiment of a medical image analyzing system of the present disclosure. The difference between the third embodiment and the aforementioned second embodiment is that the medical image analyzing system of the present disclosure may include the medical image analysis device 11 without the computer device 12 and the medical image analysis device 11 may include a display unit 118. The medical image analysis device 11 of the medical image analyzing system of the present disclosure not only may be the aforementioned mobile phone, tablet computer, notebook computer or desktop computer, server or cloud server, but also may be computed tomography (CT) equipment or magnetic resonance imaging (MRI) equipment. In other words, the medical image analyzing system of the present disclosure may be installed in CT equipment or MRI equipment, but the present disclosure is not limited thereto.

The detailed technical contents of the modules used in the medical image analyzing systems in FIG. 1A to FIG. 1C are described below.

Figure 2A:
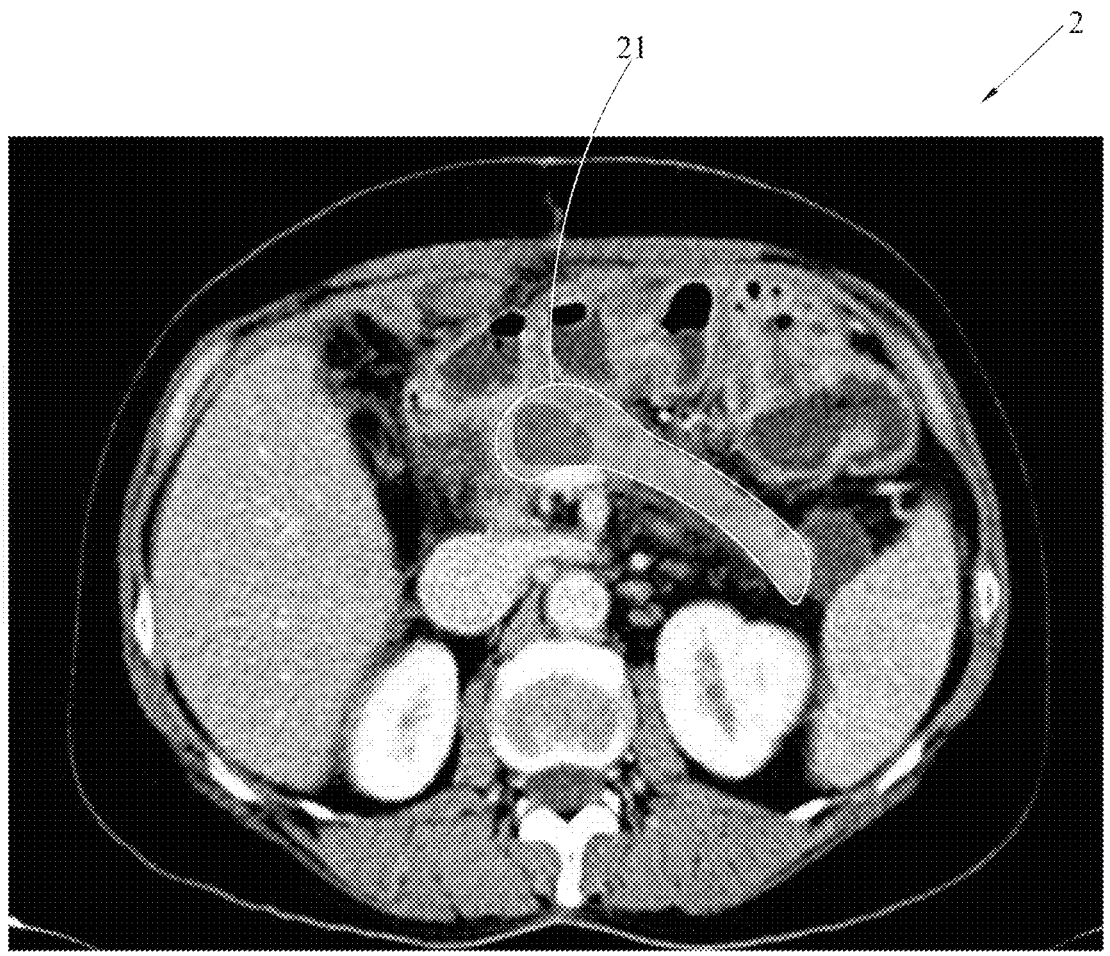
FIG. 2A is a schematic diagram illustrating a computed tomography image of a training image used by a medical image analyzing system of the present disclosure.
Figure 2B:
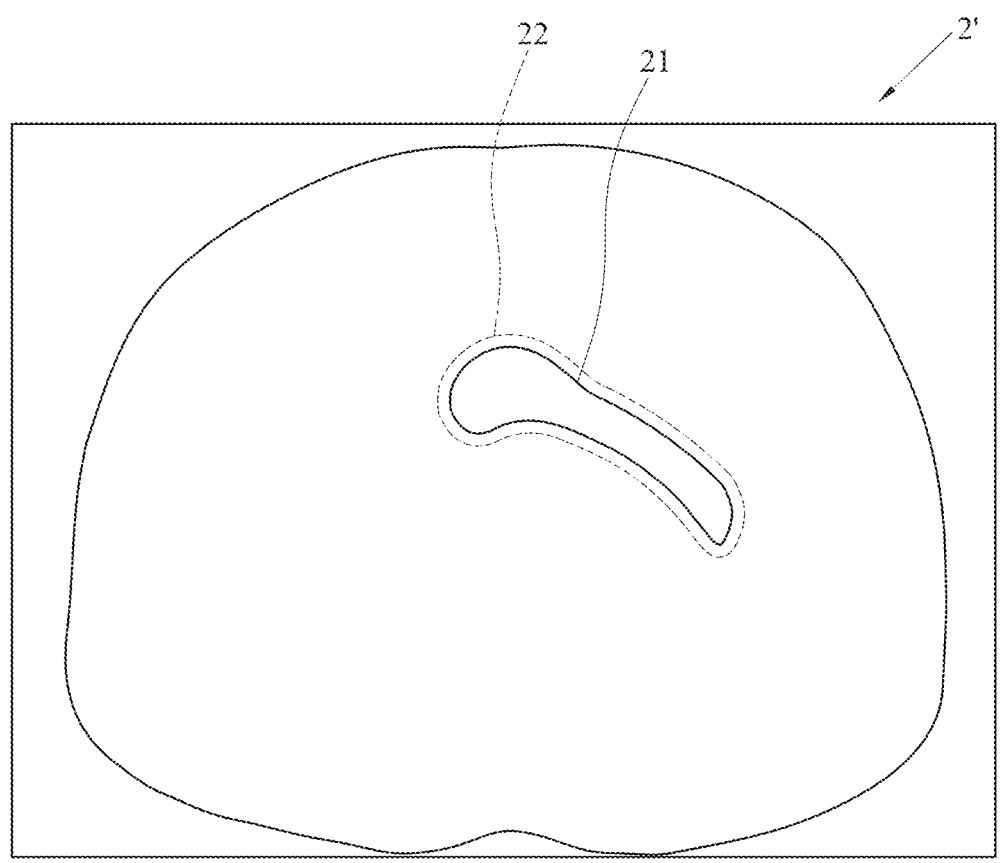
FIG. 2B to FIG. 2D are simplified schematic diagrams illustrating the image preprocessing and the generation of image patches of FIG. 2A.

FIG. 2A is a schematic diagram illustrating a computed tomography image of an image 2 used in a medical image analyzing system of the present disclosure. The organ 21 may be for example a pancreas. FIG. 2B is a simplified schematic diagram of FIG. 2A. The simplification of FIG. 2B is for the convenience of description and does not cause any limitation to the present disclosure. Referring to FIG. 2A and FIG. 2B, the image preprocessing module 111 is configured to process at least one image 2 including an organ 21 to generate at least one processed image 2′, wherein the processed image 2' includes a segmentation label 22 corresponding to the location of the organ 21. The segmentation label 22 may be generally known as the region of interest (ROI). In an embodiment, the processing of the image 2 by the image preprocessing module 111 includes reconstruction, dilation, windowing and normalization, and so on. In detail, the image 2 is a two-dimensional (2D) image or a three-dimensional (3D) image generated by CT or MRI. Taking a 2D CT image for example, a typical patient has a plurality of 2D CT images. First, linear interpolation and nearest-neighbor interpolation are used respectively to reconstruct the images into slices with a uniform thickness (e.g., 5 mm), wherein linear interpolation can target the entire images, and nearest-neighbor interpolation can target the segmentation label 22. Next, dilate the labeled area corresponding to the organ 21 in the image 2. For example, expand the boundary of the organ 21 by 3×3 pixels on the x-y plane, so as to dilate the labeled area corresponding to the organ 21 in the image 2, and the dilated labeled area will correspondingly become the segmentation label 22 in the subsequent processed image 2'. The purpose of dilating the labeled area is to prevent the case that the original labeled area is not completely aligned to the organ 21 and to increase the information generated by the module. Next, window the image 2, for example, set the window width and the window level of the image 2 to 250 and 75 Hounsfield units (HU), respectively. Finally, normalize the image 2, that is, set the pixel intensity values of the image 2 to the range from 0 to 1. The reconstructed, dilated, windowed and normalized image 2 will become the processed image 2'. In an embodiment, there are a plurality of the images 2, so there are also a plurality of the processed images 2', but the present disclosure is not limited thereto.

Figure 2C:
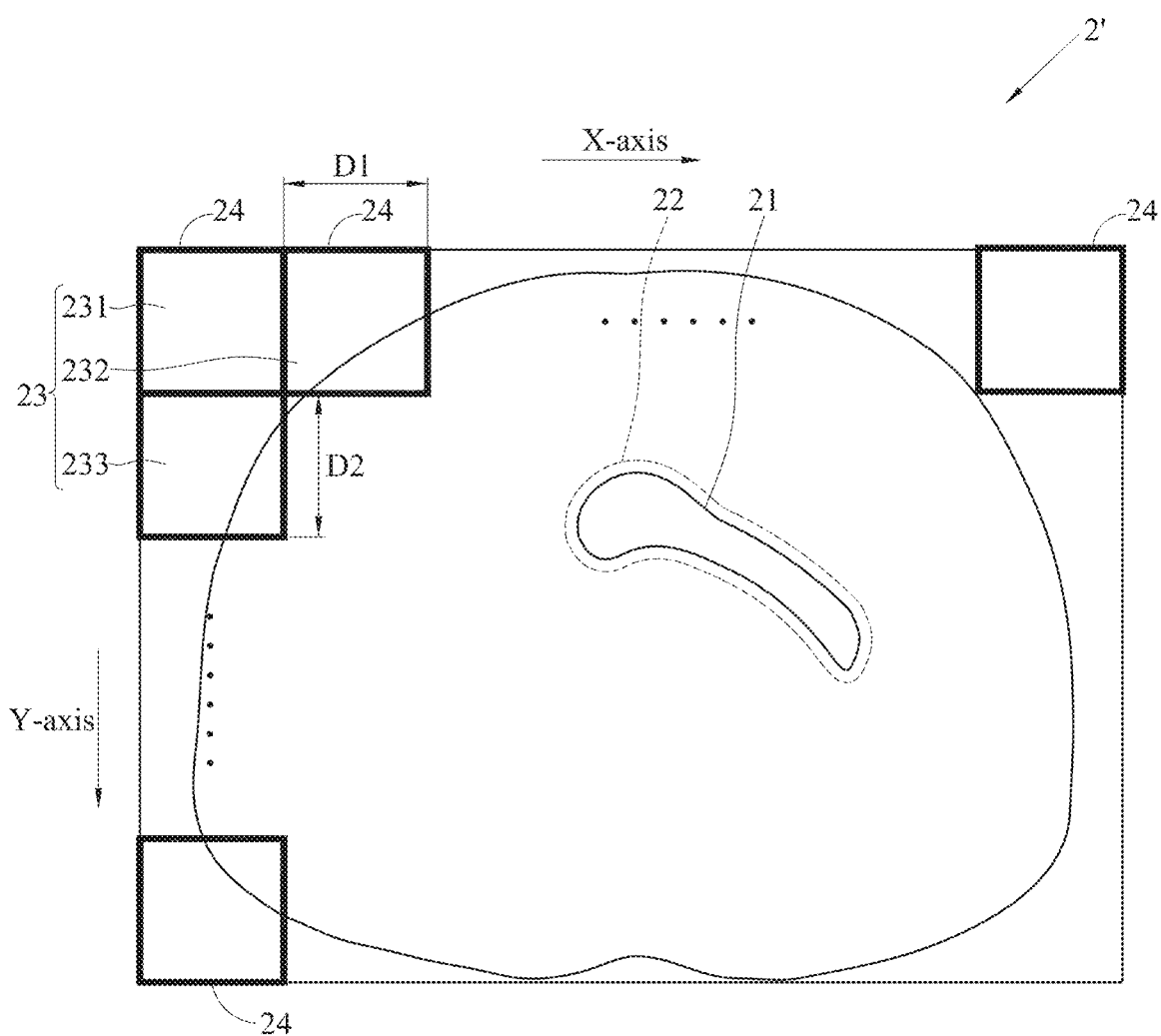

Referring to FIG. 2C, the patch cropping module 112 is configured to crop a plurality of image patches 23 from the processed image 2' including the segmentation label 22. In an embodiment, the patch cropping module 112 crops the image patches 23 from the processed image 2' according to a square window 24 moving along an x-axis and then along a y-axis of the processed image 2' including the segmentation label 22. For example, the processed image 2' may be 512×512 pixels in size and the square window 24 may be 50×50 pixels in size. Generally, the patch cropping module 112 sets the square window 24 at the left boundary and the top boundary (i.e., the top-left corner) of the processed image 2' as the starting point, and crops the image patch 231. Next, the patch cropping module 112 moves the square window 24 along the x-axis of the processed image 2' to the right by a distance D1 (e.g., 50 pixels), and then the patch cropping module 112 crops the image patch 232. The patch cropping module 112 repeats the moving and the cropping until the square window 24 reaches the right boundary of the processed image 2'. After that, the patch cropping module 112 moves the square window 24 to a location at the left boundary of the processed image 2' that is 50 pixels away from the top boundary of the processed image 2' (i.e., moving the square window 24 along the y-axis downward by a distance D2), and then the patch cropping module 112 crops the image patch 233, and then repeats the moving and the cropping until the square window 24 reaches the right boundary of the processed image 2'. Finally, the patch cropping module 112 moves the square window 24 to the right boundary and the bottom boundary (i.e., the bottom-right corner) of the processed image 2' to crop more image patches 23. In an embodiment, the patch cropping module 112 crops a lot of image patches 23 from each processed image 2', and the image patches 23 do not overlap with each other. In addition, the sizes of the processed image 2' and the square window 24 above are exemplary, and the present disclosure is not limited thereto.

In another embodiment, the patch cropping module 112 does not set the square window 24 at the left boundary and the top boundary (i.e., the top-left corner) of the processed image 2' as the starting point. Instead, the patch cropping module 112 sets the square window 24 near a location corresponding to the segmentation label 22 in the processed image 2' as the starting point, but the present disclosure is not limited thereto.

Figure 2D:
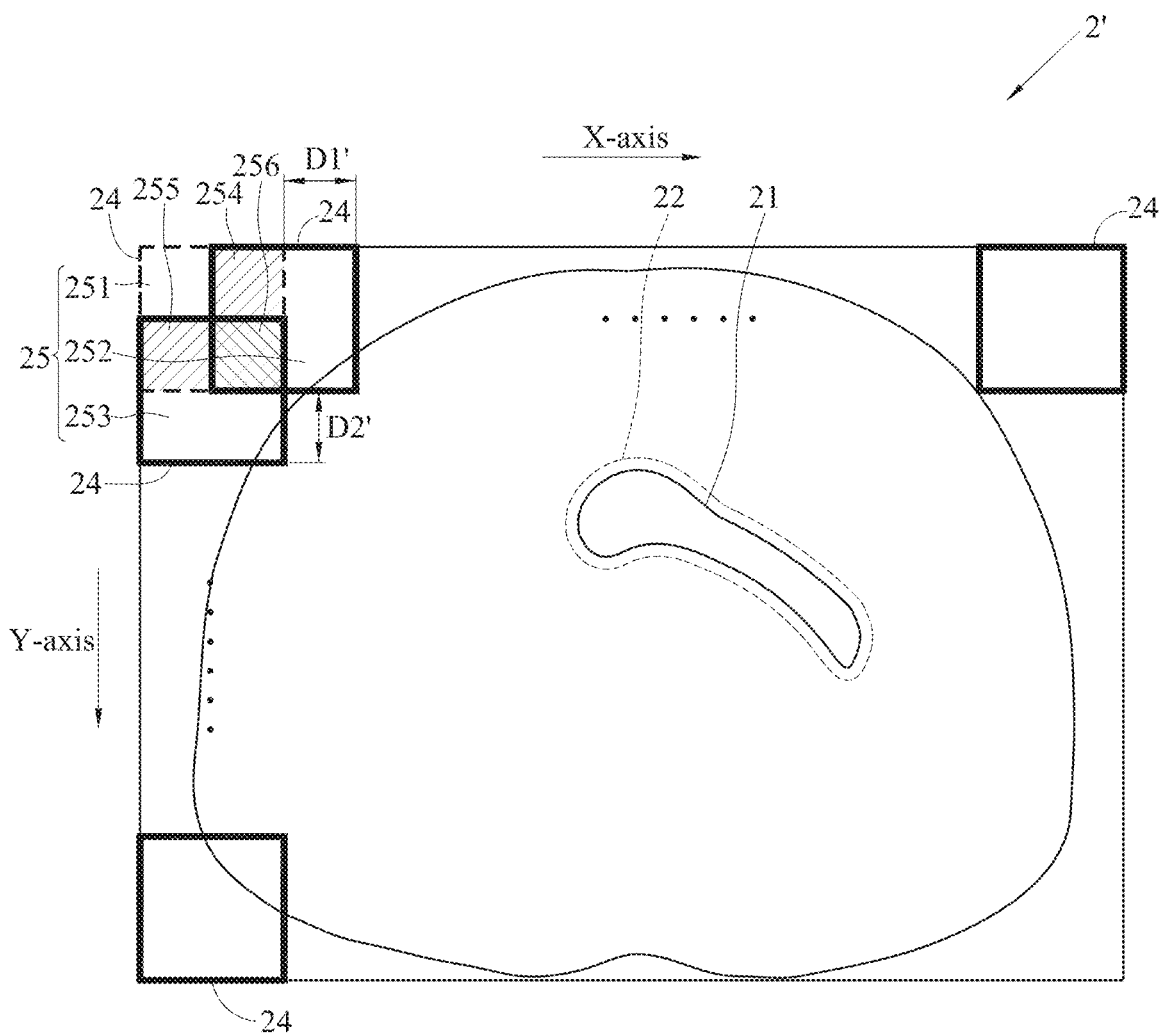

In still another embodiment, as shown in FIG. 2D, the image patches 25 cropped by the patch cropping module 112 may partially overlap with each other. In detail, the patch cropping module 112 crops the plurality of image patches 25 from the processed image 2' according to a square window 24 moving along an x-axis and then along a y-axis of the processed image 2' including the segmentation label 22. As in the aforementioned embodiment, the patch cropping module 112 may set the square window 24 at the same location at the left boundary and the top boundary (i.e., the top-left corner) of the processed image 2' as the starting point, or the patch cropping module 112 may set the square window 24 near a location corresponding to the segmentation label 22 in the processed image 2' as the starting point. This embodiment differs from the aforementioned embodiment in the moving distances D1' and D2' of the square window 24. In the aforementioned embodiment, for example, the square window 24 is 50×50 pixels in size, and the distance of each movement is 50 pixels. Therefore, the cropped image patches 23 do not overlap with each other. However, in this embodiment, for example, the square window 24 is 50×50 pixels in size, and the distance of each movement is shorter than 50 pixels. Therefore, the cropped image patches 25 partially overlap with each other. As shown in FIG. 2D, each time the square window 24 merely moves by 25 pixels (the distances D1' and D2'). Therefore, the image patches 251 and 252 have overlapping parts 254 and 256, respectively, and the ratio of the area of each overlapping part to the total area of each image patch is 50%. In addition, the image patches 251 and 253 have overlapping parts 255 and 256, respectively, and the ratio of the area of each overlapping part to the total area of each image patch is 50%. The present disclosure does not limit the moving distances of the square window 24 and the ratio of the area of the overlapping parts of the image patches. The area of the overlapping part between two image patches may range from 20% to 80% (e.g., 50%) of the total area of each image patch. The purpose of overlapping image patches is repeating the analysis by the deep learning model when the image patches are provided for training the deep learning model subsequently. For example, the overlapping parts 254 and 255 are repeatedly analyzed for 2 times, and the overlapping part 256 may be repeatedly analyzed for 3 times, in order to improve accuracy.

The image 2 mentioned in the foregoing embodiments uses CT images of diagnosed patients when training the model. In other words, the radiologist can clearly know the location of the tumor from the image 2, which enables the plurality of image patches 23 and 25 generated by the patch cropping module 112 to have cancerous labels or non-cancerous labels, respectively. As long as there is an image patch 23, 25 that covers a part of a tumor, that image patch can be tagged with a cancerous label. An image patch 23, 25 can be tagged with a non-cancerous label only when that image patch does not cover a tumor at all. In an embodiment, if a plurality of image patches 23, 25 are tagged with the non-cancerous labels and do not have the segmentation label 22, those image patches may be excluded from subsequent training and prediction process, but the present disclosure is not limited thereto.

Figure 3:
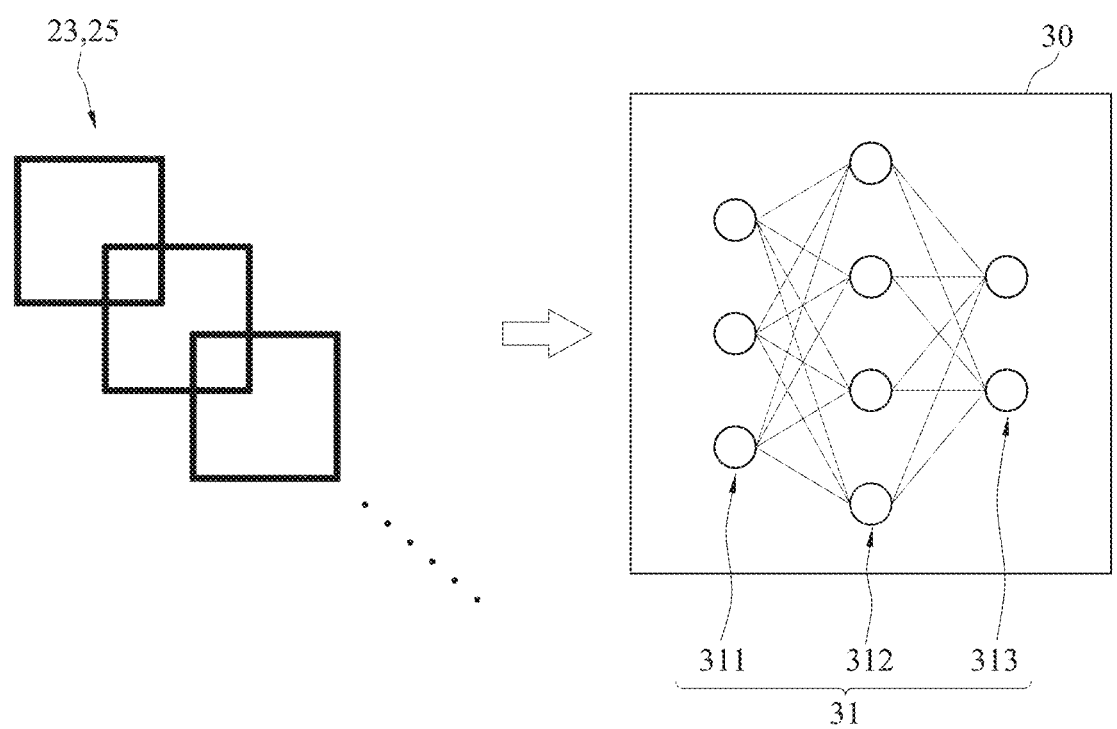
FIG. 3 is a schematic diagram illustrating the training of a deep learning model in a medical image analyzing system of the present disclosure.

Referring to FIG. 3, after obtaining the plurality of image patches 23, 25, the analysis module 113 trains a deep learning model 30 with the plurality image patches 23, 25 to obtain a plurality of first prediction values respectively corresponding to each of the plurality image patches 23, 25. In an embodiment, the analysis module 113 may use a convolution neural network 31 to train the deep learning model 30. The convolution neural network 31 generally includes a plurality of layers, such as a plurality of convolution layers 311, a plurality of pooling layers 312 and a plurality of fully-connected layers 313, etc. The present disclosure does not limit the numbers of layers of the convolution layers 311, the pooling layers 312 and the fully-connected layers 313. Moreover, the present disclosure does not require concurrently using all of the convolution layers 311, the pooling layers 312 and the fully-connected layers 313. For example, the present disclosure may use only the convolution layers 311 and the fully-connected layers 313. The present disclosure also may use only two convolution layers 311 and fully-connected layers 313, and so on.

In an embodiment, the convolution neural network 31 used by the analysis module 113 may include two convolution layers 311, followed by a rectified linear unit (ReLu) as an activation function, and then connected with the pooling layers 312 before connected with the fully-connected layers 313. After this step, the plurality of image patches 23, 25 may be respectively flatten to an array, and then the aforementioned step may be repeated, until the plurality of image patches 23, 25 are respectively flattened to a single value. The following Table 1 presents the processing of the convolution neural network 31 when the size of the plurality of image patches is 50×50 pixels.

TABLE 1

| layer | kernel size | channel | output size |
| --- | --- | --- | --- |
| convolution layer 1a | 5 × 5 | 16 | (50, 50, 16) |
| convolution layer 1b | 5 × 5 | 32 | (50, 50, 32) |
| pooling layer 1 | 2 × 2 | — | (25, 25, 32) |
| convolution layer 2a | 3 × 3 | 64 | (25, 25, 64) |
| convolution layer 2b | 3 × 3 | 64 | (25, 25, 64) |
| pooling layer 2 | 2 × 2 | — | (12, 12, 64) |
| convolution layer 3a | 3 × 3 | 128 | (12, 12, 128) |
| convolution layer 3b | 3 × 3 | 128 | (12, 12, 128) |
| pooling layer 3 | 2 × 2 | — | (6, 6, 128) |
| flatten | — | — | (4608) |
| fully-connected layer 1 | — | — | (32) |
| fully-connected layer 2 | — | — | (32) |
| fully-connected layer 3 | — | — | (1) |

In an embodiment, the convolution neural network 31 uses weighted binary cross-entropy as the loss function to account for the imbalance in the number of the image patches with the cancerous labels and the number of the image patches with the non-cancerous labels. For example, the loss function may be:

$$Loss = -\frac{1}{N}\sum_{i=1}^{N}(w_1 y_i \log(p(y_i)) + w_2(1-y_i)\log(1-p(y_i)))$$

wherein N is the total number of the image patches, $y_i$ is 1 when the i-th image patch is tagged with the cancerous label, and $y_i$ is 0 when the i-th image patch is tagged with the non-cancerous label. $p(y_i)$ is the model prediction value of the i-th image patch. The weights $w_1$ and $w_2$ are set as the inverse ratio of the number of the image patches with the cancerous labels to the number of the image patches with the non-cancerous labels. In other words, $w_1:w_2=N_{non-cancerous}:N_{cancerous}$.

In an embodiment, when the analysis module 113 uses a plurality of image patches 23, 25 to train the deep learning model 30, the analysis module 113 may set hyperparameters and add mechanisms such as callback to optimize the performance of model training. For example, the batch size, one of the hyperparameters, may be set to 2560, which means that the deep learning model 30 receives 2560 image patches in each iteration, but the present disclosure is not limited thereto. In addition, there are two callback mechanisms: one is that the analysis module 113 reduces the learning rate of the convolution neural network 31 to the deep learning model 30 if the analysis module 113 validates that the loss function does not decrease for the last ten iterations; the other one is that the analysis module 113 stops the convolution neural network 31 from training the deep learning model 30 after the analysis module 113 validates that the loss function remains stable in the last 40 iterations. However, the present disclosure is not limited to the aforementioned callback mechanisms. For example, the number of iterations is not limited.

In an embodiment, after the analysis module 113 trains the deep learning model 30, the deep learning model 30 may give a corresponding first prediction value to each image patch, and the first prediction values can be used for classification. For example, each image patch may be classified as cancerous or non-cancerous depending on whether the corresponding first prediction value exceeds a first threshold. The method for determining the first threshold is described below.

Figure 4:
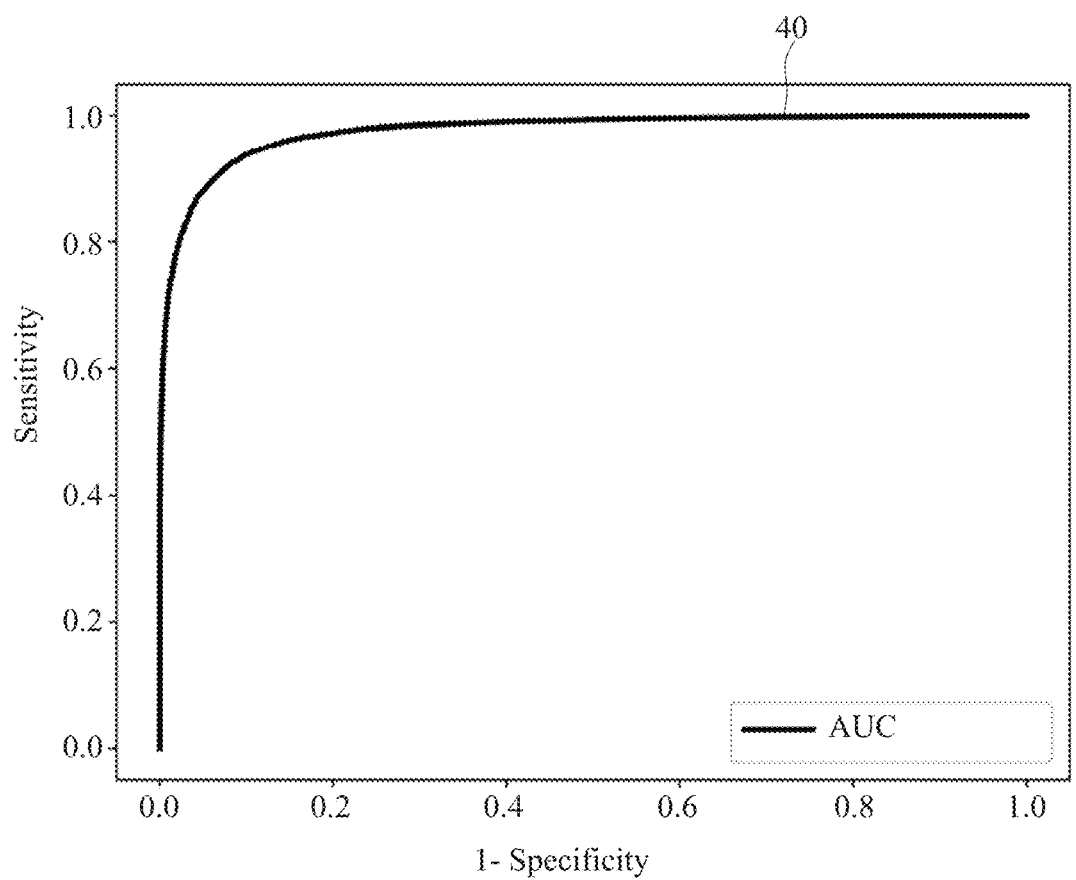
FIG. 4 is a schematic diagram illustrating a receiver operating characteristic curve plotted by a medical image analyzing system of the present disclosure.

The threshold selection module 114 can plot the first curve according to the plurality of first prediction values and determine the first threshold according to the first curve to determine whether each of the plurality of image patches 23, 25 is cancerous. In detail, the plurality of image patches 23, 25 respectively have the corresponding plurality of first prediction values. The plurality of first prediction values are determined by a specific threshold (for example, if the first prediction value is greater than the specific threshold, the corresponding image patch is determined as cancerous), and then the statistical indicators corresponding to the specific threshold, including sensitivity and specificity, etc., can be calculated. Any value between 0 and 1 (e.g., 0.1, 0.2, 0.3, 0.4 . . . etc.) is a possible value for the specific threshold. In this way, the receiver operating characteristic curve (ROC) 40 as shown in FIG. 4 can be plotted according to the plurality of sensitivities and specificities calculated based on the possible values of the plurality of specific thresholds, and the area under receiver operating characteristic curve (AUC) and statistical indicators such as a plurality of Youden indices can be obtained from the receiver operating characteristic curve 40, wherein the Youden indices (the formula is: Youden index=sensitivity−[1-specificity]) can be calculated from the sensitivity and specificity corresponding to each point in the receiver operating characteristic curve 40. In the present disclosure, the first threshold is the threshold yielding the maximum value in the plurality of Youden indices. When the first prediction value of an image patch is greater than the first threshold, the image patch may be classified as cancerous (positive). When the first prediction value of an image patch is less than or equal to the first threshold, the image patch may be classified as non-cancerous (negative).

In an embodiment, when the deep learning model of the present disclosure determines that an image patch is cancerous and the radiologist also determines that the image patch is cancerous, the image patch is defined as a true positive; when the deep learning model of the present disclosure determines that an image patch is non-cancerous and the radiologist also determines that the image patch is non-cancerous, the image patch is defined as a true negative; when the deep learning model of the present disclosure determines that an image patch is cancerous but the radiologist determines that the image patch is non-cancerous, the image patch is defined as a false positive; and when the deep learning model of the present disclosure determines that an image patch is non-cancerous but the radiologist determines that the image patch is cancerous, the image patch is defined as a false negative. The aforementioned sensitivity and specificity are defined by the following formula: sensitivity=true positive/(true positive+false negative); specificity=true negative/(true negative+false positive).

The computer-aided diagnosis module 121 is configured to input at least one patient image to the image preprocessing module 111 and the patch cropping module 112 to generate a plurality of image patches corresponding to the at least one patient image and input the plurality of image patches to the deep learning model 30 to obtain a plurality of first prediction values respectively corresponding to each of the plurality of image patches.

In detail, the computer-aided diagnosis module 121 may be specifically computer-assisted detection/diagnosis tool (CAD tool) software, and the computer-aided diagnosis module 121 may use the deep learning model 30 trained by the analysis module 113 of the medical image analysis device 11 to assist clinicians in diagnosing patients. For example, the clinician can first obtain the patient image of a patient to be analyzed, and input the patient image to the image preprocessing module 111 and the patch cropping module 112 of the medical image analysis device 11 through the computer-aided diagnosis module 121 of the computer device 12 to generate a plurality of image patches. The processing of the patient image by the image preprocessing module 111 and the patch cropping module 112 is the same as that of the aforementioned image 2. Next, input the plurality of image patches of the patient into the deep learning model 30 to obtain a plurality of first prediction values corresponding to the plurality of image patches. Next, the computer-aided diagnosis module 121 controls the threshold selection module 114 to calculate at least one second prediction value corresponding to the at least one patient image according to the plurality of first prediction values corresponding to the plurality of image patches generated from the at least one patient image. In an embodiment, a patient corresponds to the second prediction value. If a patient has a plurality of patient images, the patient still corresponds to one second prediction value. The second prediction value is calculated based on the plurality of first prediction values of the same patient. However, the present disclosure is not limited thereto. In an embodiment, after the plurality of first prediction values respectively corresponding to each of the plurality of image patches are determined by the first threshold determined by the threshold selection module 114, the threshold selection module 114 classifies the plurality of image patches as cancerous (positive) or non-cancerous (negative). The second prediction value is generated by counting the number of the image patches classified as cancerous in the at least one patient image. For example, the second prediction value may be the ratio between the number of image patches generated from at least one patient image of a patient that are classified as cancerous by applying the first threshold to the first prediction values corresponding to all of the image patches generated from the at least one patient image of the patient and the total number of all of the image patches generated from the at least one patient image of the patient, but the present disclosure is not limited thereto. In an embodiment, the computer-aided diagnosis module 121 may be configured to input a single patient image to obtain a single second prediction value for clinicians to obtain the information with which the computer-aided diagnosis module 121 determines whether the patient image is cancerous subsequently. The computer-aided diagnosis module 121 may also input a plurality of patient images (i.e., different patients) to obtain a plurality of second prediction values for plotting the second curve in order to determine the second threshold subsequently. However, the present disclosure is not limited thereto. In addition, the aforementioned single patient image may be one or more 2D CT images taken from a single patient, so that the second prediction value can correspond to a single patient image. The single patient image can also be one or more 3D CT images taken from a single patient. The one or more 3D CT images are processed by the image preprocessing module 111 to generate a plurality of 2D patient images, so that the second prediction value can also correspond to the plurality of patient images (which can also directly correspond to the patient). However, the present disclosure is not limited thereto.

Next, the computer-aided diagnosis module 121 controls the threshold selection module 114 to plot the second curve according to the plurality of second prediction values to determine the second threshold according to the second curve to determine whether each of the plurality of patient images harbors cancer. The second curve is a receiver operating characteristic curve and the second threshold is the threshold yielding the maximum value of a Youden index. The plotting of the second curve and the determination method of the second threshold are the same as those of the first curve and the first threshold. After the second threshold is determined, the computer-aided diagnosis module 121 can determine the second prediction value corresponding to the patient image according to the second threshold to determine whether the patient image is cancerous. For example, after a patient image is processed by each module and the deep learning model, the second prediction value obtained is 0.7. If the second threshold is 0.5, the computer-aided diagnosis module 121 can give the result that the patient image is cancerous. If the second threshold is 0.8, the computer-aided diagnosis module 121 can give the result that the patient image is non-cancerous.

Figure 5:
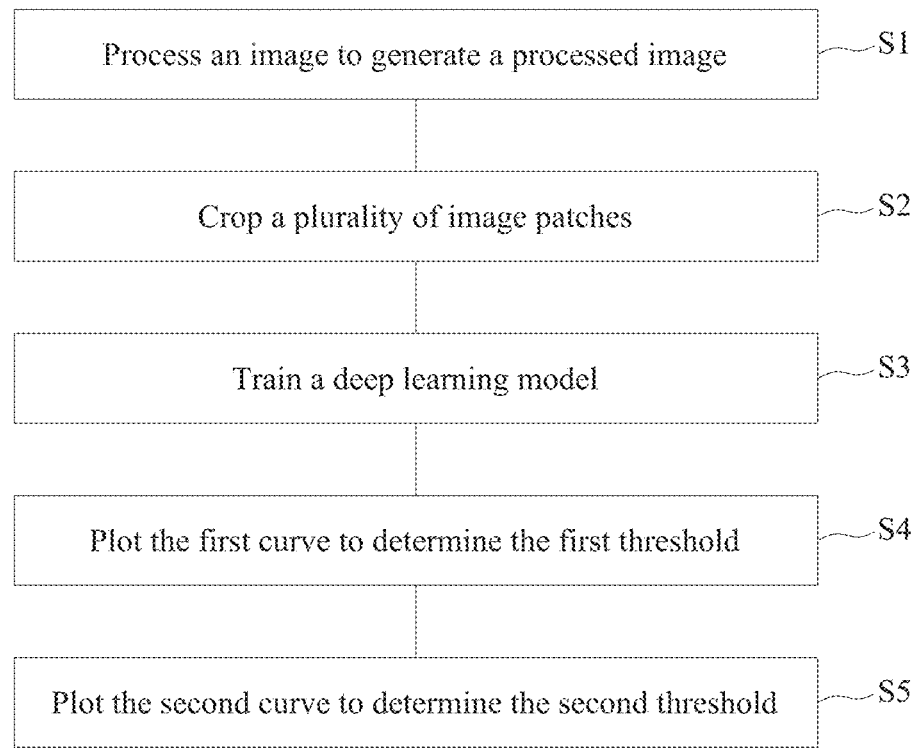
FIG. 5 is a schematic diagram illustrating a flowchart of a medical image analyzing method of the present disclosure.

Referring to FIG. 5, which discloses a schematic flow chart of the medical image analyzing method of the present disclosure, and the medical image analyzing method of the present disclosure may be used in the medical image analyzing system 1 having the medical image analysis device 11 as described above. The technical contents of the medical image analyzing method of the present disclosure are the same as those of the aforementioned medical image analyzing system.

First, the medical image analyzing method of the present disclosure may process an image to generate a processed image (step S1). That is, at first, the medical image analyzing method of the present disclosure controls the image preprocessing module 111 of the medical image analysis device 11 to process at least one image 2 including an organ 21 to generate at least one processed image 2', wherein the processed image 2' includes a segmentation label 22 corresponding to a location of the organ 21.

Next, the medical image analyzing method of the present disclosure may crop a plurality of image patches (step S2). That is, the medical image analyzing method controls the patch cropping module 112 of the medical image analysis device 11 to crop a plurality of image patches 23, 25 from the processed image 2' including the segmentation label 22.

Next, the medical image analyzing method of the present disclosure trains a deep learning model (step S3). That is, the medical image analyzing method controls the analysis module 113 of the medical image analysis device 11 to train the deep learning model 30 with a plurality of image patches to obtain a plurality of first prediction values respectively corresponding to each of the plurality of image patches.

Next, the medical image analyzing method of the present disclosure plots the first curve to determine the first threshold (step S4). That is, the medical image analyzing method controls the threshold selection module 114 of the medical image analysis device 11 to plot the first curve according to the plurality of first prediction values and determine the first threshold according to the first curve to determine whether each of the plurality of image patches 23, 25 is cancerous.

Finally, after training the deep learning model and determining the first threshold, the medical image analyzing method of the present disclosure may plot the second curve to determine the second threshold (step S5). That is, the medical image analyzing method controls the computer-aided diagnosis module 121 of the computer device 12 electrically connected to the medical image analysis device 11 (FIG. 1A) or the computer-aided diagnosis module 121 in the medical image analysis device 11 (FIG. 1B) to input at least one patient image to the image preprocessing module 111 and the patch cropping module 112 to generate a plurality of image patches, and input the plurality of image patches into the deep learning model 30 to obtain a plurality of first prediction values respectively corresponding to the plurality of image patches. The computer-aided diagnosis module 121 further controls the threshold selection module 114 to calculate at least one second prediction value corresponding to at least one patient image according to the plurality of first prediction values respectively corresponding to the plurality of image patches, and plot the second curve based on at least one second prediction value to determine whether the at least one patient image harbors cancer, wherein the second curve is a receiver operating characteristic curve and the second threshold is a threshold yielding the maximum value of the Youden index. In an embodiment, for each of the at least one second prediction value, the second prediction value may be the ratio between the number of image patches generated from at least one patient image of a patient that are classified as cancerous by applying the first threshold to the first prediction values corresponding to all of the image patches generated from the at least one patient image of the patient and the total number of all of the image patches generated from the at least one patient image of the patient, but the present disclosure is not limited thereto.

Among the deep learning models trained by the medical image analyzing system and the corresponding method of the present disclosure, the model trained with image patches of 50×50 pixels (i.e., the size of the square window is 50×50 pixels) has better performance. It is clear from Table 2 below that the sensitivity, the specificity, the accuracy and the AUC of the image patch size of 50×50 pixels are respectively 91.1±2.0%, 86.5±2.6%, 87.3±1.9%, and 0.96±0.001. If the image patch size is smaller than 50×50 pixels, the AUC drops, which may be because the image patch size is too small to contain enough information about the tumor and adjacent tissues. If the image patch size is larger than 50×50 pixels, the stability of the AUC is insufficient, which may be related to that larger image patches introduce more noises. As such, the image patch size of 50×50 pixels is one preferred choice.

TABLE 2

| image patch size (pixels) | sensitivity | specificity | accuracy | AUC |
| --- | --- | --- | --- | --- |
| 10 × 10 | 80.5 ± 1.9% | 81.8 ± 2.4% | 81.6 ± 1.7% | 0.89 ± 0.001 |
| 30 × 30 | 88.1 ± 1.5% | 85.4 ± 1.7% | 85.9 ± 1.2% | 0.95 ± 0.002 |
| 50 × 50 | 91.1 ± 2.0% | 86.5 ± 2.6% | 87.3 ± 1.9% | 0.96 ± 0.001 |
| 70 × 70 | 91.5 ± 1.8% | 86.7 ± 3.1% | 87.4 ± 2.4% | 0.96 ± 0.009 |

In addition, the efficacy of the medical image analyzing system and the corresponding method of the present disclosure is confirmed as follows: firstly provide 244,859 image patches with cancerous labels of 295 patients with pancreatic cancer, and provide 1,216,715 image patches with non-cancerous labels of 256 patients without pancreatic cancer as training data for deep learning models. The aforementioned image patches are randomly divided into a training group and a verification group. When the deep learning model trained by the image patches of the training group is used to distinguish the image patches with cancerous labels from the image patches with non-cancerous labels in the verification group, the area under the receiver operating characteristic curve (AUC) is as high as 0.96, and the sensitivity, the specificity and the accuracy are 91.3%, 84.5% and 85.6% respectively. The AUC for distinguishing between patients with cancer and patients without cancer is 1.00, and the sensitivity, the specificity and the accuracy are 97.3%, 100% and 98.5%, respectively.

Furthermore, the comparison between radiologists and the medical image analyzing system and the corresponding method of the present disclosure is confirmed as follows: 75 images of patients with cancer and 64 images of patients without cancer were used to test the aforementioned deep learning model obtained based on the training data. The deep learning model shows that the AUC for distinguishing between patients with cancer and patients without cancer by the medical image analyzing system of the present disclosure is 0.997, and the sensitivity, the specificity and the accuracy are respectively 97.3%, 100.0% and 98.6%. In the same images, the sensitivity of the radiologists is merely 94.4%.

Moreover, 101 images of patients with cancer and 88 images of patients without cancer were used to test the deep learning model obtained based on the training data. The deep learning model shows that the AUC in distinguishing between patients with cancer and patients without cancer by the medical image analyzing system of the present disclosure is 0.999, and the sensitivity, the specificity and the accuracy are 99.0%, 98.9% and 98.9% respectively. In the same images, the sensitivity of the radiologists is merely 91.7%.

After counting and calculating the tumor size of the aforementioned cancer patients and the sensitivity of the medical image analyzing system and the corresponding method of the present disclosure and the radiologists, it is known that the sensitivity of the present disclosure in detecting tumor sizes larger than 4 cm and between 2-4 cm is 100%, while the sensitivity of radiologists in detecting tumor sizes larger than 4 cm is 100% and the sensitivity of radiologists in detecting tumor sizes between 2-4 cm is merely 90.8%. In addition, the sensitivity of the present disclosure in detecting tumor sizes smaller than 2 cm is 92.1%, whereas the sensitivity of radiologists in detecting tumor sizes smaller than 2 cm is merely 89.5%.

In summary, the medical image analyzing system and the corresponding method of the present disclosure have a higher sensitivity compared to radiologists in identifying pancreatic cancer, which means that the medical image analyzing system and the method thereof of the present disclosure can effectively assist radiologists to reduce the clinical misdiagnosis rate, especially in the case of small tumors. Therefore, the medical image analyzing system and the method thereof of the present disclosure can effectively improve the general clinical situation that about 40% of pancreatic cancers smaller than 2 cm are not detected.

The aforementioned embodiments are merely illustrative of the technical principles, features and effects of the present disclosure, and are not intended to limit the scope of implementation of the present disclosure. Any person skilled in the art can modify and change the aforementioned embodiments within the spirit and scope of the present disclosure. However, any equivalent modifications and changes made using the content taught by the present disclosure should still be covered by the following claims. The scope of protection of the rights of the present disclosure shall be as listed in the following claims.

What is claimed is:

1. A medical image analyzing system, comprising:
    an image preprocessing module, executed by a processor, configured to process at least one image comprising an organ to generate at least one processed image, wherein the processed image comprises a segmentation label corresponding to a location of the organ;
    a patch cropping module, executed by the processor, configured to crop a plurality of image patches from the processed image comprising the segmentation label;
    an analysis module, executed by the processor, configured to train a deep learning model with the image patches to obtain a plurality of first prediction values respectively corresponding to each of the image patches;
    a threshold selection module, executed by the processor, configured to plot a first curve according to the first prediction values and determine a first threshold according to the first curve to determine whether each of the image patches is cancerous; and
    a computer-aided diagnosis module, executed by the processor, configured to input at least one patient image to the image preprocessing module and the patch cropping module to generate a plurality of patient image patches and input the patient image patches to the deep learning model to obtain a plurality of first prediction values corresponding to each of the patient image patches respectively;
    wherein the computer-aided diagnosis module controls the threshold selection module to calculate at least one second prediction value corresponding to the at least one patient image according to the first prediction values corresponding to the patient image patches generated from the at least one patient image and plot a second curve according to the at least one second prediction value to determine a second threshold according to the second curve to determine whether the at least one patient image harbors cancer.

2. The medical image analyzing system of claim 1, wherein the patch cropping module crops the image patches from the processed image according to a square window moving along an x-axis and a y-axis of the processed image comprising the segmentation label.

3. The medical image analyzing system of claim 2, wherein the image patches do not overlap with each other or the image patches partially overlap with each other.

4. The medical image analyzing system of claim 3, wherein an area of an overlapping part between two of the image patches ranges from 20% to 80% of a total area of each of the image patches.

5. The medical image analyzing system of claim 1, wherein the analysis module uses a convolution neural network to train the deep learning model.

6. The medical image analyzing system of claim 1, wherein the first curve is a receiver operating characteristic curve and the first threshold is a threshold yielding a maximum value of a Youden index.

7. The medical image analyzing system of claim 1, wherein the image is a two-dimensional image or a three-dimensional image generated by computed tomography or magnetic resonance imaging.

8. The medical image analyzing system of claim 1, wherein, for each of the at least one second prediction values, the second prediction value is a ratio between a number of the patient image patches generated from the at least one patient image of a patient that are classified as cancerous by applying the first threshold to the first prediction values corresponding to all the patient image patches generated from the at least one patient image of the patient and a total number of all the patient image patches generated from the at least one patient image of the patient.

9. The medical image analyzing system of claim 1, wherein the second curve is a receiver operating characteristic curve and the second threshold is a threshold yielding a maximum value of a Youden index.

10. A medical image analyzing method, comprising:
    processing at least one image comprising an organ to generate at least one processed image, wherein the processed image comprises a segmentation label corresponding to a location of the organ;
    cropping a plurality of image patches from the processed image comprising the segmentation label;
    training a deep learning model with the image patches to obtain a plurality of first prediction values respectively corresponding to each of the image patches;
    plotting a first curve according to the first prediction values and determining a first threshold according to the first curve to determine whether each of the image patches is cancerous;
    inputting at least one patient image to generate a plurality of patient image patches;
    inputting the patient image patches to the deep learning model to obtain a plurality of first prediction values corresponding to each of the patient image patches respectively;
    calculating at least one second prediction value corresponding to the at least one patient image according to the first prediction values corresponding to the patient image patches generated from the at least one patient image; and
    plotting a second curve according to the at least one second prediction value to determine a second threshold according to the second curve to determine whether the at least one patient image harbors cancer.

11. The medical image analyzing method of claim 10, wherein the cropping of the image patches is based on a square window moving along an x-axis and a y-axis of the processed image comprising the segmentation label.

12. The medical image analyzing method of claim 11, wherein the image patches do not overlap with each other or the image patches partially overlap with each other.

13. The medical image analyzing method of claim 12, wherein an area of an overlapping part between two of the image patches ranges from 20% to 80% of a total area of each of the image patches.

14. The medical image analyzing method of claim 10, wherein the training of the deep learning model comprises using a convolution neural network to train the deep learning model.

15. The medical image analyzing method of claim 10, wherein the first curve is a receiver operating characteristic curve and the first threshold is a threshold yielding a maximum value of a Youden index.

16. The medical image analyzing method of claim 10, wherein the image is a two-dimensional image or a three-dimensional image generated by computed tomography or magnetic resonance imaging.

17. The medical image analyzing method of claim 10, wherein, for each of the at least one second prediction values, the second prediction value is a ratio between a number of the patient image patches generated from the at least one patient image of a patient that are classified as cancerous by applying the first threshold to the first prediction values corresponding to all the patient image patches generated from the at least one patient image of the patient and a total number of all the patient image patches generated from the at least one patient image of the patient.

18. The medical image analyzing method of claim 10, wherein the second curve is a receiver operating characteristic curve and the second threshold is a threshold yielding a maximum value of a Youden index.

* * * * *